US006569421B2

(12) United States Patent
Hodges

(10) Patent No.: US 6,569,421 B2
(45) Date of Patent: May 27, 2003

(54) TREATMENT OF BRAIN DAMAGE

(75) Inventor: Helen Hodges, London (GB)

(73) Assignee: Reneuron Limited (GB)

( * ) Notice: Subject to any disclaimer, the term of this patent is extended or adjusted under 35 U.S.C. 154(b) by 0 days.

(21) Appl. No.: 09/537,617

(22) Filed: Mar. 29, 2000

(65) Prior Publication Data

US 2002/0037277 A1 Mar. 28, 2002

(30) Foreign Application Priority Data

Mar. 29, 1999 (GB) .............................................. 9907243

(51) Int. Cl.$^7$ ......................... A61K 48/00; A61K 35/30; C12N 5/10
(52) U.S. Cl. .................. 424/93.2; 424/93.21; 424/93.7; 435/325; 435/352; 435/354; 434/362
(58) Field of Search ............................... 424/93.7, 93.2, 424/93.21; 128/732; 435/240.2, 240.1, 325, 354, 352; 434/362

(56) References Cited

U.S. PATENT DOCUMENTS

| | | | |
|---|---|---|---|
| 4,690,142 A | * | 9/1987 | Ross et al. |
| 5,270,191 A | | 12/1993 | McKay et al. |
| 5,750,376 A | * | 5/1998 | Weiss et al. |
| 5,753,491 A | * | 5/1998 | Major et al. |
| 5,753,506 A | * | 5/1998 | Johe |
| 5,851,832 A | * | 12/1998 | Weiss et al. |
| 5,958,767 A | | 9/1999 | Snyder et al. |
| 6,197,585 B1 | | 3/2001 | Stringer |
| 6,200,806 B1 | | 3/2001 | Thomson |

FOREIGN PATENT DOCUMENTS

| | | | |
|---|---|---|---|
| WO | 9109936 | | 7/1991 |
| WO | 9301275 | | 1/1993 |
| WO | 9615226 | | 5/1996 |
| WO | WO 97/10329 | * | 3/1997 |
| WO | 9927076 | | 11/1998 |
| WO | WO 00/20560 | * | 4/2000 |

OTHER PUBLICATIONS

Shihabuddin et al. Experimental Neurology (1996), 139(1): 61–72. Selective hippocampal lisions differentially affect teh phenotypic fate of transplanted neuronal precursor cells.*
Synder et al., Curr. Opin. Neurol. 9: 126–136. Central nervous system cell transplantation: a novel therapy for storage diseases?, 1996.*
Synder et al., Proc. Nat'l. Scad. Sci. USA 94(21): 11663–1168. Multipotent neural precursors can differentiate toward replacement of neurons undergoing targeted apoptotic degeneration in adult mouse neocortex, Oct. 14, 1997.*
Synder et al., Cell 68: 33–51. Multipotent neural cell lines can engraft and participate in development of mouse cerebellum, Jan. 10, 1992.*
Sinden et al., Neuroscience, vol. 81: 3, pp 599–608. Recovery of spatial learning by grafts of a conditionally immortalized hippocampal neuroepithelial cell line into the ishcaemia–lesioned hippocampus., 1997.*
Scheffler et al., Trends in Neuroscience, vol. 22: 8, pp 348–357. Marrow–mindedness: a perceptive on neuropoiesis, 1999.*
Sandberg et al., Nucleic Acids Symposium Series, Proceedings of the 1998 Miami Bio/Technology Winter Symposium, No. 38, pp 139–142. Cellular therapeutic approaches for neurodegenerative disorders, Feb. 1998.*
Hodges et al., Pharmacology Biochemistry and Behavior, vol. 56: 4, pp 763–780. Cognitive deficits induced by global cerebral ischaemia: Prospects for transplant therapy, 1997.*
McKay et al. (1990) "Mechanisms regulating Cell Number and Type in the Mammalian Central Nervous System" Cold Spring Harbor Symposia on Quantitaive Biology, vol. 55, pp. 291–301.
McKay et al. (1993) "Immortalized Stem Cells From the Central Nervous System" C.R. Acad. Sci. Paris, Sciences De La Vie, vol. 316, pp. 1452–1457.
Netto et al. (1993) *Behavioral Brain Res.* vol. 58, pp. 107–112.
Okabe et al. (1996) "Development of Neuronal Precursor Cells and Functional Postmitotic Neurons from Embryonic Stem Cells In Vitro" Mechanisms of Development, vol. 59, pp. 89–102.
Rashid–Doubell et al. (1994) *Gene Therapy* vol. 1, Suppl. 1, p. S63.

\* cited by examiner

*Primary Examiner*—Gary Kunz
*Assistant Examiner*—Stephen Gucker
(74) *Attorney, Agent, or Firm*—Saliwanchik, Lloyd & Saliwanchik

(57) ABSTRACT

The present invention relates to the treatment of brain damage by cellular transplantation. According to one aspect of the invention, a method for treating a motor, sensory and/or cognitive deficit comprises administering a composition comprising pluripotent cells into the damaged brain in a region contra-lateral to that containing the site of damage. The cells are preferably conditionally immortal.

15 Claims, No Drawings

TREATMENT OF BRAIN DAMAGE

FIELD OF THE INVENTION

This invention relates to the treatment of disorders associated with damage to the brain. In particular, this invention relates to treatment of disorders by cellular transplantation into a damaged brain.

BACKGROUND OF THE INVENTION

Stroke is the largest cause of adult disability worldwide. The incidence of stroke is about 1.3% of the US population, and 39.4% of victims show significant residual impairments, ranging from hemiplegia to restricted limb use and speech defects. Approximately 60% of strokes are caused by occlusion of the middle cerebral artery (MCAo), resulting in damage in the striatum and cortex with consequent deficits to sensory and motor systems. There is therefore a substantial clinical need for treatments that reduce or alleviate the deficits.

Typical therapies for stroke are aimed at interrupting the cascade of events that lead to intraneuronal calcium accumulation and cell death, and to provide stimulation through rehabilitation, e.g. physiotherapy, to promote intracerebral reorganisation. However, pharmacological treatments must be administered quickly to protect against cell death that typically occurs within three hours of occlusion. In addition, the therapy based on rehabilitation appears to be limited to a period of 3–6 months after stroke, after which residual disabilities do not undergo appreciable reduction.

There has been much interest recently in the possibility of transplanting new cells into the damaged neuronal system to promote repair and alleviate the disorders. One difficulty associated with cell transplantation is the need to provide clonal cell lines from different regions of the brain. This has proved to be a major difficulty in preparing cells for transplantation. WO-A-97/10329 describes the use of conditionally immortalised pluripotent neuroepithelial cells in the transplantation into the damaged brain. The neuroepithelial cells express a temperature-sensitive oncogene so that they are capable of unlimited expansion under permissive low temperatures in vitro, but cease dividing to develop into mature neural cells on implantation into the higher temperature of the brain (38° C). A particular advantage of these cells has been shown to be their ability to develop into site-appropriate neurons or glia, under the control of signals from the host brain, so that problems associated with choosing the correct tissue for transplantation is avoided. It has also been shown that the cells can migrate to the site of damage when transplanted into a region proximal to the damaged site. Therefore, the use of these cells offers a viable alternative to pharmacological treatments for repair of brain damage.

However, although the cells were shown to migrate to discrete areas of damage, focal ischaemia results in extensive damage and it is by no means certain that areas of infarction would provide a sufficiently well vascularised matrix to support the survival of grafted cells.

There is therefore the need for improvements in transplantation in order to provide cells that successfully graft into the adult damaged brain and compensate for the deficits.

SUMMARY OF THE INVENTION

It has now been realised that pluripotent cells can successfully repair damage when administered into the side of the brain contra-lateral to that containing the site of damage.

Therefore, according to one aspect of the invention there is a method for treating brain damage comprising administering a composition comprising pluripotent cells into the damaged brain, wherein administration is into the brain hemisphere contra-lateral to that containing the site of damage.

Preferably, the pluripotent cells are neuroepithelial stem cells, in particular, those from the MHP36 clonal cell line, defined herein.

The cells are preferably conditionally immortal. Immortalisation may be achieved by the transduction of a temperature-sensitive oncogene into the cells as disclosed in WO-A-97/10329.

The advantage of administering the cells contra-laterally is that the intact (contra-lateral) region may provide a more tolerant environment for cell grafts, avoiding the inflammatory response at the site of damage which might cause cell rejection.

DESCRIPTION OF THE INVENTION

The cells of the present invention are capable of correcting a sensory, motor and/or cognitive deficit when implanted into the brain hemisphere contra-lateral to that of the damaged part of the human brain. The term "damage" used herein includes reduction or loss of function caused by cell loss. Damage may be caused by any of a variety of means including physical trauma, hypoxia (lack of oxygen), chemical agents, for example, damage may be caused by drug abuse, and disease. The following diseases and pathological conditions are examples of diseases or conditions which result in deficits which may be treated in accordance with the present invention: traumatic brain injury, stroke, perinatal ischaemia, including cerebral palsy, Alzheimer's, Pick's and related dementing neurodegenerative diseases, multiple sclerosis, multi-infarct dementia, Parkinson's and Parkinson's-type diseases, Huntington's disease, Korsakoff's disease and Creuzfeld-Jacob disease. Amnesia, particularly following transitory global ischaemia such as after cardiac arrest or coronary bypass surgery, may also be treated in accordance with the present invention.

The present invention is particularly suited to the treatment of stroke where damage occurs primarily in one brain hemisphere e.g. due to an occlusion in the middle cerebral artery.

By "contra-lateral" it is intended that this refers to the hemisphere of the brain that does not contain the site of damage. Therefore, if there is an occlusion in the left hemisphere, then, obviously, the contra-lateral region is the right, undamaged, hemisphere.

Of course, in some instances damage may occur in both hemispheres, and in these cases the contra-lateral region is understood to be the hemisphere which exhibits least damage.

The term "pluripotent" is used herein to denote an undifferentiated cell that has the potential to differentiate into different types or different phenotypes of cell, in particular into cells having the appropriate phenotype for the intended use. The cell type or phenotype into which such a pluripotent cell finally differentiates is at least partly dependent on the conditions in which the cell exists or finds itself.

For use in the present invention the cells should be capable of differentiating into cells appropriate to repair or compensate for damage or disease in the target area of the brain. It will be appreciated that cells for transplantation need not be capable of differentiating into all types or phenotypes of neural cells. The cells may, for example, be bipotent. However, a high degree of potency is generally preferred as this gives greater flexibility and potential for transplantation into different areas of the brain.

Suitable pluripotent cells include those known in the art as "stem cells" and those called or known as "precursor cells". In particular, neuroepithelial stem cells are suitable for use in the present invention. However, other cells may also be used. Alternative cells may be those defined as haematopoietic stem cells which may be capable of differentiating into neural cells.

The pluripotent neuroepithelial cells are advantageously, and will generally be, conditionally immortal and may be prepared as disclosed in WO-A-97/10329.

The treatment may be carried out on any mammal but the present invention is especially concerned with the treatment of humans, especially treatment with human cells, and with human cells and cell lines.

To treat a patient it is necessary to establish where damage has occurred in the brain. This may be carried out by any method known in the art, e.g. magnetic resonance imaging (MRI). Once the existence of damage has been established, whether it be in one isolated area or in several areas, treatment by implantation of cells into the contra-lateral region to that of the damaged area may be carried out, again by conventional means. The pluripotent cells may be transplanted at a single site, or preferably at multiple sites, and may be able to migrate to the site(s) of damage and, once there, differentiate in response to the local microenvironment, into the necessary phenotype or phenotypes to improve or restore function.

In addition to administering the cells into the contra-lateral region, it may also be desirable to co-administer the cells into the damaged hemisphere (ipsi-lateral region). Treatment in this manner may promote the improvement or restoration of brain function by different mechanisms.

Without wishing to be bound by theory, it may be that repair following transplantation into the contra-lateral region results from migration of the pluripotent cells into the area of damage, with the reconstitution of local circuits to restore or sustain function. It may also be that the transplanted cells augment spontaneous processes within the intact (contra-lateral) side which attempt to compensate for the damage. If the latter is correct, then it may be unnecessary for the transplanted cells to cross to the side of damage to exert an effect.

It may be possible to promote repair by encouraging the activity of particular regions of the brain. By using passive or active exercise of certain regions, it may be possible to augment the spontaneous processes occurring after transplantation. For example, it should be possible to stimulate particular brain regions by requiring certain tasks to be performed. In doing so, the brain region may generate biological signals that aid repair.

The stimulation of the brain may be visualised using detection techniques such as magnetic resonance imaging (MRI). These techniques can be adapted to permit the patient to visualise the active brain regions, so that, through the process of biofeedback, the patient can stimulate particular regions that may encourage repair.

Preferably, treatment will substantially correct a motor, sensory and/or cognitive deficit. However, that may not always be possible. Treatment according to the present invention and with the cells, medicaments and pharmaceutical preparations of the invention, may lead to improvement in function without complete correction. Such improvement will nevertheless be worthwhile and of value.

The number of cells to be used will vary depending on the nature and extent of the damaged tissue. Typically, the number of cells used in transplantation will be in the range of about one hundred thousand to several million. Treatment need not be restricted to a single transplant. Additional transplants may be carried out to further improve function.

Methods for transplantation of cells into humans and animals are known to those in the art and are described in the literature in the art. The term "transplantation" used herein includes the transplantation of cells which have been grown in vitro, and may have been genetically modified, as well as the transplantation of material extracted from another organism. Cells may be transplanted by implantation by means of microsyringe infusion of a known quantity of cells in the target area where they would normally disperse around the injection site. Suitable excipients and diluents will be apparent to the skilled person, based on formulations used in conventional cell transplantation.

The following non-limiting example illustrates the invention.

EXAMPLE

Conditionally immortal pluripotent neuroepithelial cells from the MHP 36 clonal cell line were prepared as disclosed in WO-A-97/10329.

In the experiments described below, conditionally immortal cells used for transplantation are derived from the $H-2K^b$-tsA58 transgenic mouse developed by M. Noble and his associates at the Ludwig Institute for Cancer Research (Jat et al., P.N.A.S. USA, 1991, 88:5096). All cells from this mouse possess a temperature-sensitive oncogene (tsA58, the temperature sensitive mutant of the SV40 large T antigen under the control of the interferon-inducible $H-2K^b$ promotor) such that the cells divide at the permissive temperature (lower than body temperature, 33° C.) but differentiate only when restored to mouse body temperature (38° C.–39° C.). It is this feature that provides them with conditional immortality. This allowed us to clone and expand cell lines in vitro which then differentiated upon transplantation into a host brain. A number of cell lines were cloned from a population of cells taken originally from the transgenic mouse, specifically, from embryonic day 14 (E 14) hippocampus. We studied the rats, which received transplants of those cells, for at least 8 months and in no case did the cells, after transplantation, form tumors. Furthermore, in post-mortem histological preparations, the transplanted cells (marked by prior transfection with a lac-z reporter gene) have the appearance of differentiated cells appropriate to the rodent nervous system.

21 Wistar rats were subjected to left intraluminal occlusion of the middle cerebral artery (MCAo-IL) under halothane anaesthesia as disclosed in Ginsberg et al, Cerebrovascular disease, 1998; Volume 1:14–35.

Following exposure of the left internal carotid artery, a 3.0 mm proline filament coated at the tip with silicon was inserted 18–20 mm up to the junction of the circle of Willis and tied in place for 60 min. Anaesthesia was discontinued after insertion of the filament, and the rat tested for neurologic deficit (contra-lateral paw flexion and circling) to establish the presence of ischaemia. Anaesthesia was resumed after 60 min for retraction of the filament to the external carotid stump, where it was left in place, the excess filament trimmed off, and the wound sutured. Neurologic and health status were monitored for a week, until normal feeding was seen and post-operative weight regained. Control rats (n=11) were sham operated by exposure of the left internal carotid artery only.

Transplant and sham graft surgery was undertaken 2–3 weeks after occlusion or sham surgery. Rats were anaesthetised with Immobilon (0.01 ml/100 g, im) after pre-treatment with Hypnovel (midazolam: 0.03 ml/100, im), and placed in a stereotaxic frame. Holes were drilled in the right side of the skull to allow the penetration of a 10 µl Hamilton syringe at the following coordinates (mm) derived from Bregma, with the skull in the flat position (−3.2 mm). AP represents "anterior-posterior", L represents "lateral" and V represents "ventral".

| | | |
|---|---|---|
| AP: −0.3 | L: −3.5 | V: −4.5, −6.0 |
| | L: −5.5 | V: −4.0, −5.5 |
| AP: −1.3 | L: −3.0 | V: −5.0, −6.5 |
| | L: −5.5 | V: −5.0, −6.5 |

3.0 µl of suspension (25,000 cells/µl) were infused over 2 min at each of the 8 sites, and the cannula was left in place for a further 2 min to allow diffusion from the tip. Medial descents were aimed for striatum and lateral descents were aimed for cortex at the estimated anterior and posterior extent of the area of infarct on the opposite side, to target potential regions of reorganisation. Controls received infusions of vehicle.

Rats were tested from 4–6 weeks after transplantation over a period of 10 months. During this time the performance on the repeated measure test (Bilateral Asymmetry Test) remained stable.

Bilateral Asymmetry Test

The bilateral asymmetry test (BAT) has been used to access a variety of lesions (Schallert et al, Pharmacol. Biochem. Behaviour, 1982; 16:455–462). Strips of tape 1 cm wide and 5 cm long were wound round each of the two forepaws, in random order. Animals were placed in an observation cage and timed for latency to contact and to remove each tape. The side first contacted was also noted by the Experimenter blind as to the experimental groups. Random checks on reliability were included by comparing the Experimenter's scores with those of a second observer; typically inter-rater reliability was above 90%. Rats were tested before surgery, and during the week before grafting, to establish pre- and post-operative baselines. One session of 4 tests of 3 min was carried out each week, for 18 weeks, commencing 4–6 weeks after transplantation to assess long term recovery.

Rotation

This is a test for measuring rotational bias. When challenged with amphetamine, MCAO animals show a clear bias to the direction of the lesion.

Spontaneous and drug-induced rotation was measured approximately 38 weeks after transplantation in an 8-bowl rotameter (TSE GmbH, Bad Hamburg) in which rats were harnessed for 30 min and swivels recorded in either left or right direction. Rats were tested for response to saline (baseline). They were then tested once a week, on alternate weeks, with either amphetamine (Sigma: 2.5 mg/kg) or apomorphine (Sigma: 0.5 mg/kg) on three occasions over a testing time of 6 weeks. All injections were given in a volume of 1.0 ml/kg, ip.

Before occlusion, rats did not show a mean difference in paw use as judged by the latency to contact and removal of tapes from the left and right paw. After sham surgery the controls continued to show no preference. However, rats subjected to MCAO showed a marked disparity between the two paws, with the right paw contacted and the tape removed significantly more slowly than the left, indicative of contra-lateral sensorimotor impairment. This robust and stable deficit persisted throughout the 18 weeks of testing. In rats that received MHP36 grafts, the stroke-induced forepaw disparity was non-significant by 8 weeks after transplantation, and this improvement persisted through the 18 weeks of testing, so that there was no difference between paws. Hence grafted rats did not differ from controls as both groups showed that the two paws were equivalent in latency to contact and remove the tape, and that the right paw was contacted first as often as the left. In a group of rats that were subjected to 60 min MCAO and which did not receive sham transplants, the paw disparity was comparable to that in the group injected on the intact side with a large volume of vehicle. This result suggests that injection damage on the intact side neither exacerbated nor reduced the extent of sensorimotor deficit induced by MCAO.

Baseline (spontaneous) rotation was mildly asymmetrical in stroke rats without grafts, in that there was more turning to the right than the left, whereas control and grafted rats showed comparable turning in both directions. However, in response to amphetamine on weeks 2, 4, and 6 of testing, stroke rats without grafts showed marked turning to the left, towards the lesioned side, indicative of asymmetric dopamine release on the intact side. Group differences were very substantial and the non grafted group differed significantly from the grafted and control groups, which did not differ in response to amphetamine. A similar, but less marked effect, was seen with the postsynaptic dopamine agonist apomorphine. Groups differed on weeks 3, 5 and 7 with the non-grafted stroke group showing more marked leftwards rotation than the grafted and control groups which did not show a turning bias. In all groups the number of turns was lower in response to saline than to the dopamine agonists. However all groups showed a similar activation in response to drug, so that drug induced changes in bias in the non-grafted group were not associated with differences in activity.

At the end of behavioural testing (approximately 11 months post-transplantation) histology studies were undertaken. Rats were perfused with 4% paraformaldehyde, flushed through the upper body vasculature via a cannula inserted through the heart and into the aorta, which was attached to a pump. 50 µm coronal sections were cut through the brain, placed on gelatine-coated slides and frozen to prevent dehydration. Serial sections were stained for the presence of β-Gal labelled cells, and cells reactive to glial fibrillary acidic protein (GFAP) and tyrosine hydroxylase (TH) to identify glial and neuronal cell types within the graft.

In a first study, only one brain from the grafted and non-grafted groups subjected to MCAO was examined. In both animals subjected to MCAO, cavitation was severe, amounting to approximately 75% of the hemisphere volume. Ventricles on the infarct side were enlarged, so that only a thin strip of striatal tissue separated the lateral from the infarct. Ventricles were also enlarged to a lesser extent on the intact side, and distortion, possible via oedema soon after occlusion, had pushed the midline towards the intact side. In the grafted animal β-Gal positive cells were seen at the injection site in the middle of the intact striatum. Cells were also seen in a diagonal band stretching caudally and laterally through the striatum towards the parietal cortex. β-Gal positive cells were seen approaching and within the side opposite to implantation. They formed in a dense band along the lower ventricular margin of the corpus callosum, and encircled the area of the infarct. They were particularly prominent in the residual strip of striatum, and some had left the corpus callosum caudally to enter the cortex. These grafted cells showed morphologies of several types, including bipolar cells, glial cells and neuronal cells of both pyramidal and medium spiny neuron appearance, suggesting a diverse pattern of differentiation.

For estimating lesion volume 50 μm sections were cut from 3.7 to 6.3 mm before bregma in all rats subjected to MCAO, with and without grafts, and intact controls. Every tenth section was collected giving an inter-section distance of 500 μm and a total of 20 sections per brain. Sections were strained with Cresyl Fast Violet. Images of each section were taken using a stereo microscope and estimations of lesion volume were carried out. For control rats there was no difference between the hemispheres. In rats subjected to 60 min of MCAO there was a substantial infarct representing approximately 26% of the total brain volume. In stroke rats with MHP36 grafts, lesion volume was decreased to approximately 16% of the total brain volume, and was significantly smaller (p<0.05) than in rats with MCAO and sham grafts.

A later study compared the effect of grafts into either the ipsi-lateral or contra-lateral sides, or into the ventricles. Grafted cells were labelled with the fluorescent marker PKH26 to assist their identification. Behaviour was measured for 12 weeks after transplantation. Over this period there was a significant improvement in the bilateral asymmetry test in rats with grafts in both the ipsi-lateral and contra-lateral side, but not in those with intraventricular grafts. However, rats with intraventricular grafts, unlike those with intraparenchymal grafts, showed improved spatial learning and memory in the water maze. These results indicate that the site of grafting affects behavioural recovery and support the claim that use of multiple sites may be advantageous. In contrast to the finding in the earlier study, where contra-lateral grafts restored spontaneous and amphetamine-induced rotation in animals tested 10 months after transplantation, there was no improvement in rotation bias in any of the grafted groups tested 10–12 weeks after grafting. These findings suggested that the time course of recovery may differ for different tasks.

The brains of all the rats were processed for histology as described above. Grafted cells were visualised by PKH26 fluorescence, and double labelled with antibodies to neuronal and glial markers to identify cells that differentiated into these phenotypes. Site of implantation influenced cell survival and the pattern of migration. In general, more cells survived with grafts implanted contra-lateral to the lesion than into the ventricles, with ipsi-lateral grafts being intermediate. However, there was a similar proportion of neuronal cells, seen primarily in the midline regions, in all granted groups. Importantly, grafts from all three sites migrated across the midline to the opposite side of the brain. Thus about a third of grafted cells placed in the lesioned side were found in the intact side of the brain, whilst a similar proportion of grafted cells also migrated from the intact to the lesioned side, as in the earlier study. These surprising findings indicated that grafted cells not only responded to signals arising from injury, but were also attracted to the intact side, possibly by signals arising from processes of reorganisation.

Lesion volume, measured as described above, showed that the area of damage comprised approximately 18% of the total brain volume. However there was no difference between sham grafted animals with MCAO, and those with grafts. Thus grafts did not significantly reduce lesion volume, measured 14 weeks after transplantation, in contrast to the reduction seen at 11 months after transplantation in the earlier study. This may indicate that grafts give some protection against secondary degeneration, and the effect is only clearly evident at a late time point.

In a later study, the remaining brains were sectioned and the lesion volumes determined for each group by measuring the volumes of the ipsi-lateral and contra-lateral hemisphere. Volume measurements of the lesion size revealed 18% loss of total brain volume in animals with 60 minutes MCAO. No difference in lesion size was found between the MCAo groups regardless of transplantation site. When the total number of transplanted cells was analysed according to implantation site, it emerged that grafted cells implanted contra-laterally were significantly greater than those grafted in the ventricles, although there was no statistical difference when compared to cells grafted ipsi-laterally. It was also apparent that there had been extensive migration away from the implantation site into the opposite hemisphere.

The above experiments aimed to see whether grafts of MHP36 cells, from a conditionally immortalised clonal line, would promote functional recovery from stroke damage when placed in the intact hemisphere contra-lateral to the infarct cavity. The findings indicated that both sensorimotor and motor asymmetries were normalised in rats with grafts initially sited in the intact hemisphere.

The evidence for recovery of sensorimotor and motor functions is robust, because improvements were seen over an extended time period. For example, in MCA-occluded rats without grafts, tape-removal deficits were seen consistently over an 18 week period of testing, with no hint of spontaneous recovery. Improvement in grafted rats was also consistent over this period. The late rotational data is interesting in that spontaneous deficits were manifest in mild rotation to the right, possibly reflecting a stronger push by the unaffected left paw, relative to the right. However, dopamine agonist drugs induced marked rotation to the left, consistent with activation of dopamine receptors on the right (intact) side of the brain. This asymmetry was not evident in rats with grafts sited in the intact side, even though one might expect the asymmetry to be amplified, if grafted cells on the intact side differentiated into tyrosine hydroxylase-positive (TH) neurons.

The control, grafted and non-grafted stroke groups showed a similar degree of locomotor stimulation in response to amphetamine (i.e. the number of rotations increased substantially above baseline) so that the drug affected activity in all groups. If the normalisation of rotation bias in the grafted group reflected lesion-induced insensitivity to dopamine stimulation on both sides of the brain, one would not expect to see such a marked increase in rotation in response to amphetamine. Therefore it is reasonable to suppose that MHP36 grafts normalised rotational behaviour by providing dopaminergic inervation on the side of the infarct. However, since this is a late effect, some other compensatory mechanism, possibly involving reduced retrograde degeneration, cannot be excluded.

There was some evidence of grafted cells on the side of implantation, not only around the sites of injection, but also forming a ventral stream of migration through the striatum. Thus it may be premature to conclude that grafted cells exert functional effects only if they cross to the side of damage. They may also be involved in reorganisation of the intact hemisphere. This conclusion is supported by finding that cells implanted on the lesion side migrated to the intact contra-lateral side.

What is claimed is:

1. A method for treating a cognitive deficit in a mammal caused by brain damage, said method comprising administering pluripotent cells into a damaged mammalian brain, wherein said damage is primarily in one hemisphere and said administration is into the brain hemisphere contra-lateral to the brain hemisphere containing the primary site of damage, wherein said pluripotent cells are hippocampal mouse cells comprising a gene encoding the tsA58 mutant of the SV40 large T antigen under the control of an H-2K$^b$ promoter, wherein said pluripotent cells are capable of differentiating into neural cells, and wherein said pluripotent cells are administered in an amount effective to improve cognitive function.

2. The method, according to claim 1, wherein brain damage is associated with stroke.

3. The method, according to claim 1, wherein said pluripotent cells are neuroepithelial stem cells.

4. The method, according to claim 1, wherein said pluripotent cells are from the MHP36 clonal cell line.

5. The method, according to claim 1, wherein the brain is stimulated by exercise after administering the pluripotent cells.

6. The method, according to claim 5, wherein said exercise is augmented by bio-feedback.

7. The method, according to claim 1, wherein said pluripotent cells are administered only into the brain hemisphere contra-lateral to the brain hemisphere containing the primary site of damage.

8. The method, according to claim 1, wherein said pluripotent cells are administered at multiple sites into the brain hemisphere contra-lateral to the brain hemisphere containing the primary site of damage.

9. The method, according to claim 1, wherein said pluripotent cells are administered into an undamaged area of the brain.

10. The method, according to claim 1, wherein said pluripotent cells are administered intraparenchymally.

11. The method, according to claim 1, wherein said pluripotent cells are administered intraparenchymally into an undamaged area of the brain.

12. The method, according to claim 7, wherein said pluripotent cells are administered into an undamaged area of the brain.

13. The method, according to claim 7, wherein said pluripotent cells are administered intraparenchymally.

14. The method, according to claim 7, wherein said pluripotent cells are administered intraparenchymally into an undamaged area of the brain.

15. The method, according to claim 1, wherein said pluripotent cells are derived from an H-2K$^b$-tsA58 transgenic mouse.

* * * * *